United States Patent [19]

Krause et al.

[11] Patent Number: 4,853,149

[45] Date of Patent: Aug. 1, 1989

[54] HETEROCYCLIC LIQUID CRYSTAL COMPOUNDS

[75] Inventors: Joachim Krause, Dieburg; Andreas Wächtler, Griesheim, both of Fed. Rep. of Germany; Bernhard Scheuble, Yokohama, Japan; Georg Weber, Erzhausen, Fed. Rep. of Germany

[73] Assignee: Merck Patent Gesellschaft Mit Beschränkter Haftung, Darmstadt, Fed. Rep. of Germany

[21] Appl. No.: 112,165

[22] Filed: Oct. 26, 1987

[30] Foreign Application Priority Data

Oct. 25, 1986 [DE] Fed. Rep. of Germany ....... 3636370

[51] Int. Cl.$^4$ .................. C09K 3/34; C07D 333/78; C07D 307/935; C07D 209/94; C07D 277/60; C07D 235/02; C07D 263/52
[52] U.S. Cl. .................. 252/299.61; 252/299.01; 252/299.5; 350/350 R; 350/350 S; 548/165; 548/169; 548/170; 548/173; 548/179; 548/180; 548/152; 548/221; 548/224; 548/217; 548/323; 548/465; 548/466; 548/512; 548/513; 548/514; 548/515; 548/516; 548/450; 548/517; 548/518; 549/52; 549/54; 549/55; 549/56; 549/49; 549/57; 549/58; 549/465
[58] Field of Search ........... 252/299.61, 299.5, 299.01; 250/350 R, 350 S; 548/165, 169, 170, 173, 179, 180, 152, 221, 224, 217, 323, 465, 466, 512, 514, 515, 516, 452, 517, 518; 549/52, 54, 55, 56, 57, 58, 49, 465

[56] References Cited

U.S. PATENT DOCUMENTS

| | | | |
|---|---|---|---|
| 4,156,000 | 5/1979 | Teulon | 544/146 |
| 4,639,328 | 1/1987 | Krause et al. | 252/199.61 |
| 4,659,503 | 4/1987 | Eidenslhink et al. | 252/299.61 |

FOREIGN PATENT DOCUMENTS 55151077  11/1980  Japan .............................. 252/299.61

OTHER PUBLICATIONS

Karamysheva, L. A. et al., Mol. Cryst. Liq. Cryst., vol. 67, pp. 241–252 (1981).
Pavluchened, A. I., Mdl. Cryt. Liq. Cryst., vol. 37, pp. 35–46, (1976).
Zaschke, H., Advances in Liquid Crystal Research & Applications, Bata, L. Ed., Peagamon Press, Oxford, pp. 1059–1074 (1980).
Demus, D. et al., Flussige Cristalle in Tabellen II, Veb Deutscher Verlag fur Grundstoffindustrie, Leipzig, pp. 352–361, 393–397 (1984).

Primary Examiner—Teddy S. Gron
Attorney, Agent, or Firm—Millen, White & Zelano

[57] ABSTRACT

Heterocyclic liquid crystal compounds containing the structural element

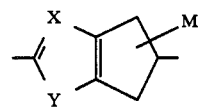

A wherein
M is H, CN,, NCS, halogen or an alkyl group with 1–5 C atoms,
X is CR$^4$ or N,
Y is CHR$^4$, O, S or NR$^5$,
R$^4$ is H, alkyl with 1–15 C atoms, halogen or cyano and
R$^5$ is H or alkyl with 1–15 C atoms,
with the proviso that in the case where Y=CHR$^4$, X is N, are suitable as components of liquid crystal phases.

12 Claims, No Drawings

HETEROCYCLIC LIQUID CRYSTAL COMPOUNDS

The invention relates to heterocyclic liquid crystal compounds.

SUMMARY OF THE INVENTION

It is an object of this invention to provide new stable liquid crystal or mesogenic compounds which are suitable as components of liquid crystal phases.

Upon further study of the specification and appended claims, further objects and advantages of this invention will become apparent to those skilled in the art.

These objects have been achieved by providing heterocyclic liquid crystal compounds which contain the structural element A.

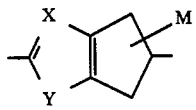

wherein

M is H, CN, NCS, halogen or an alkyl group with 1-5 C atoms,

X is $CR^4$ or N,

Y is $CHR^4$, O, S or $NR^5$, $R^4$ is H, alkyl with 1-15 C atoms, halogen or cyano and $R^5$ is H or alkyl with 1-15 C atoms, with the proviso that in the case where Y=$CHR^4$, X is N.

For simplicity, in the following text Cy is a 1,4-cyclohexylene group, Dio is a 1,3-dioxane-2,5-diyl group, Dit is a 1,3-dithiane-2,5-diyl group, Bi is a 1,4-bicyclo(2,2,2) octylene group, Pip is a piperidine-1,4-diyl group, Phe is a 1,4-phenylene group, Pyr is a pyrimidine-2,5-diyl group and Pyn is a pyridazine-3,6-diyl group, it being possible for Cy and/or Phe and/or Pyr and/or Pyn to be unsubstituted or substituted by one or more F and/or Cl atoms and/or $CH_3$ groups and/or CN groups. Dec furthermore denotes a decahydronaphthalene-2,6-diyl group and Tet denotes a 1,2,3,4-tetrahydronaphthalene-2,6-diyl group, it being possible for Dec and/or Tet to be unsubstituted or substituted by CN.

The compounds containing the structural element A can be used as components of liquid crystal phases, in particular for displays based on the principle of the twisted cell, the guest-host effect, the effect of deformation of aligned phases, the effect of dynamic scattering or the SSFLC principle.

It has been found that liquid crystal compounds containing the structural element A are outstandingly suitable as components of liquid crystal phases. In particular, stable liquid crystal phases with a broad mesophase range and a comparatively low viscosity can be prepared with the aid of these compounds.

Liquid crystal compounds above and below are to be understood as those compounds which are in themselves liquid crystal compounds, and also those compounds which form monotropic phases and therefore are of great importance as additives for liquid crystal mixtures.

The compounds of the formula I containing the structural element A are furthermore distinguished by particularly advantageous values for the ratio of the elastic constants.

By providing the compounds of the formula I, the range of liquid crystal substances which are suitable from various technological viewpoints for the preparation of liquid crystal mixtures is also quite generally considerably increased.

The compounds of the formula I have a wide field of application. Depending on the selection of the substituents, these compounds can be used as base materials from which liquid crystal phases are predominantly composed; however, it is also possible for compounds of the formula I to be added to liquid crystal base materials of other classes of compound, for example in order to influence the dielectric and/or optical anisotropy of such a dielectric. The compounds of the formula I are furthermore suitable as intermediates for the preparation of other substances which can be used as constituents of liquid crystal dielectrics.

The compounds of the formula I are colorless the pure state and form liquid crystal mesophases in a temperature range which is advantageously located for electrooptical use. They are very stable to chemicals, heat and light.

The invention thus relates to heterocyclic liquid crystal compounds containing the structural element A. The invention also relates to heterocyclic compounds having the structure wing group-ring-(bridge member-ring)$_{(1-3)}$-wing group, wherein at least one ring represents the structural element A. This structure represents the typical build-up of liquid crystal compounds. All the structural elements known to the expert are suitable here for the wing groups, rings and bridge members. A whole series of such suitable wing groups, rings and bridge members is described by D. Demus et al. in "Flüssige Kristalle in Tabellen" ("Liquid Crystals in Tables"), VEB Deutscher VerLag für Grundstoffindustrie, Leipzig 1984.

Wing group, ring and bridge member here are to be understood not only as the elements described in the abovementioned and other literature but also as similar substances which are suitable.

The invention moreover relates to heterocyclic compounds of the formula I

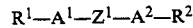

wherein $R^1$ and $R^2$ each independently of one another are an unsubstituted alkyl group of 1-15 C atoms, or such an alkyl group wherein one or two $CH_2$ groups are replaced each by one of the groups —O—, —C—, —CH-Halogen—, —CH—CN—, —O—CO—, —CO—O— or —CH=CH—, two hetero atoms not being linked directly to one another, and one of the radicals $R^1$ and $R^2$ can also be H, F, Cl, Br, —CN, —NCS or $R^3$—$(A^3)_p$—$Z^2$—, $A^1$ is —A—, —$A^4$—$Z^3$—A— or —A—$Z^3$—$A^4$—, $A^2$, $A^3$ are each 1,4-phenylene which is unsubstituted and $A^4$ or substituted by one or more F and/or Cl atoms and/or $CH_3$ groups and/or CN groups, wherein one or two CH groups can also be replaced by N atoms, 1,4-cyclohexylene which is unsubstituted or substituted by one or more F and/or Cl atoms and/or $CH_3$ groups and/or CN groups, wherein one or two non-adjacent CH$_2$ groups can also be replaced by O atoms and/or S atoms, piperidine-1,4-diyl, 1,4-bicyclo(2,2,2)-octyl-ene or decahydronaphthalene-2,6-diyl or 1,2,3,4-tetrahydronaphthalene-2,6-diyl either of which is unsubstituted or substituted by CN, $Z^1$, $Z^2$ are each —CO—O—, —O—CO—, —OCH$_2$—, —CH$_2$O—, and $Z^3$ —CH$_2$CH$_2$—, substituted ethylene or a single bond, $R^3$ is H, an unsubstituted alkyl group of 1–15 C atoms, or such an alkyl group wherein one or two CH$_2$ groups are replaced each by one of the groups —O—, —CO—, —CHHalogen—, —CH—CN—, —O—CO—, —CO—O— or —CH=CH—, two hetero atoms not being linked directly to one another, F, Cl, Br, —NCS or —CN, p is 1 or 2 and A is the structural element

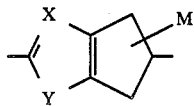

wherein

M is H, Cn, NCS, halogen or an alkyl group with 1–5 C atoms,

X is CR$^4$ or N,

Y is CHR$^4$, O, S or NR$^5$,

R$^4$ is H, alkyl with 1–15 C atoms, halogen or cyano and

R$^5$ is H or alkyl with 1–15 C atoms, and wherein, for p=2, the groups A$^3$ can be identical or different, with the proviso that in the case where Y=CHR$^4$, X is N.

The invention also relates to the use of these heterocyclic liquid cyrstal compounds as components of liquid crystal phases. The invention moreover relates to liquid crystal phases containing at least one compound according to the invention, and to electrooptical display elements containing such phases.

Above and below, R$^1$, R$^2$, R$^3$, A$^1$, A$^2$, A$^3$, A$^4$, A, Z$^1$ and Z$^2$ have the meaning given, unless explicity stated otherwise.

The compounds of the formula I accordingly include compounds of the part formulae Ia to Iay:

| | |
|---|---|
| R$^1$—A—Z$^1$—A$^2$—R$^2$ | Ia |
| R$^1$—A—A$^2$—R$^2$ | Ib |
| R$^1$—A$^4$—Z$^3$—A—Z$^1$—A$^2$—R$^2$ | Ic |
| R$^1$—A$^4$—A—A$^2$—R$^2$ | Id |
| R$^1$—A$^4$—A—Z$^1$—A$^2$—R$^2$ | Ie |
| R$^1$—A$^4$—Z$^3$—A—A$^2$—R$^2$ | If |
| R$^1$—A—Z$^1$—A$^2$—Z$^2$—A$^3$—R$^3$ | Ig |
| R$^1$—A—A$^4$—A$^2$—R$^2$ | Ih |
| R$^1$—A—Z$^3$—A$^4$—A$^2$—R$^2$ | Ii |
| R$^1$—A—A$^2$—Z$^2$—A$^3$—R$^3$ | Ij |
| R$^3$—A$^3$—A$^3$—Z$^2$—A—Z$^1$—A$^2$—R$^2$ | Ik |
| R$^3$—A$^3$—A$^4$—Z$^3$—A—Z$^1$—A$^2$—R$^2$ | Il |
| R$^3$—A$^3$—A$^3$—Z$^2$—A—A$^2$—R$^2$ | Im |
| R$^3$—A$^3$—A$^4$—A—A$^2$—R$^2$ | In |
| R$^3$—A$^3$—A$^3$—A—Z$^1$—A$^2$—R$^2$ | Io |
| R$^1$—A—Z$^1$—A$^2$—Z$^2$—A$^3$—A$^3$—R$^3$ | Ip |
| R$^1$—A—A$^2$—A$^3$—A$^3$—R$^3$ | Iq |
| R$^1$—A—Z$^1$—A$^2$—A$^3$—A$^3$—R$^3$ | Ir |
| R$^1$—A—A$^2$—Z$^2$—A$^3$—A$^3$—R$^3$ | Is |
| R$^3$—A$^3$—Z$^2$—A$^4$—Z$^3$—A—Z$^1$—A$^2$—R$^2$ | It |
| R$^1$—A$^4$—A—Z$^1$—A$^2$—Z$^2$—A$^3$—R$^3$ | Iu |
| R$^3$—A$^3$—Z$^2$—A$^4$13 A—Z$^1$—A$^2$—R$^3$ | Iv |
| R$^1$—A$^4$—A—A$^2$—Z$^2$—A$^3$—R$^3$ | Iw |
| R$^1$—A—Z$^3$—A$^4$—Z$^1$—A$^2$—Z$^2$—A$^3$—R$^3$ | Ix |
| R$^1$—A—Z$^3$—A$^4$—A$^2$—Z$^2$—A$^3$—R$^3$ | Iy |
| R$^1$—A—A$^4$—Z$^1$—A$^2$—Z$^2$—A$^3$—R$^3$ | Iz |
| R$^1$—A—A$^4$—A$^2$—Z$^2$—A$^3$—R$^3$ | Iaa |
| R$^1$—A—Z$^3$—A$^4$—Z$^1$—A$^2$—Z$^2$—A$^3$—A$^3$—R$^3$ | Iab |
| R$^1$—A—Z$^3$—A$^4$—Z$^1$—A$^2$—A$^3$—A$^3$—R$^3$ | Iac |
| R$^1$—A—Z$^3$—A$^4$—A$^2$—Z$^2$—A$^3$—A$^3$—R$^3$ | Iad |
| R$^1$—A—A$^4$—Z$^1$—A$^2$—Z$^2$—A$^3$—A$^3$—R$^3$ | Iae |
| R$^1$—A—A$^4$—A$^2$—A$^3$—A$^3$—R$^3$ | Iaf |
| R$^1$—A—Z$^3$—A$^4$—A$^2$—A$^3$—A$^3$—R$^3$ | Iaq |
| R$^1$—A—A$^4$—Z$^1$—A$^2$—A$^3$—A$^3$—R$^3$ | Iah |
| R$^1$—A—A$^4$—A$^2$—Z$^2$—A$^3$—A$^3$—R$^3$ | Iai |
| R$^3$—A$^3$—A$^3$—Z$^2$—A$^4$—Z$^3$—A—Z$^1$—A$^2$—R$^2$ | Iaj |
| R$^1$—A$^4$—Z$^3$—A—Z$^1$—A$^2$—A$^3$—A$^3$—R$^3$ | Iak |
| R$^1$—A$^4$—Z$^3$—A—A$^2$—Z$^2$—A$^3$—A$^3$—R$^3$ | Ial |
| R$^1$—A$^4$—A—Z$^1$—A$^2$—Z$^2$—A$^3$—A$^3$—R$^3$ | Iam |
| R$^3$—A$^3$—A$^3$—A$^4$—A—A$^2$—R$^2$ | Ian |
| R$^1$—A$^4$—A—A$^2$—Z$^2$—A$^3$—A$^3$—R$^3$ | Iao |
| R$^1$—A$^4$—Z$^3$—A—A$^2$—A$^3$—A$^3$—R$^3$ | Iap |
| R$^3$—A$^3$—A$^3$—A$^4$—Z$^3$—A—A$^2$—R$^2$ | Iaq |
| R$^3$—A$^3$—A$^3$—A—A$^4$—A$^2$—R$^2$ | Iar |
| R$^3$—A$^3$—A$^3$—Z$^2$—A—Z$^3$—A$^4$—Z$^1$—A$^2$—R$^2$ | Ias |
| R$^3$—A$^3$—A$^3$—Z$^2$—A—A$^4$—Z$^1$—A$^2$—R$^2$ | Iat |
| R$^3$—A$^3$—A$^3$—Z$^2$—A—Z$^3$—A$^4$—A$^2$—R$^2$ | Iau |
| R$^3$—A$^3$—A$^3$—A—Z$^3$—A$^4$—Z$^1$—A$^2$—R$^2$ | Iav |
| R$^3$—A$^3$—A$^3$—Z$^2$—A—A$^4$—A$^2$—R$^2$ | Iaw |

$$R^3-A^3-A^3-A-Z^3-A^4-A^2-R^2 \quad \text{Iax}$$

$$R^3-A^3-A^3-A-A^4-Z^1-A^2-R^2 \quad \text{Iay}$$

The compounds of the part formulae Ia, Ib, Ie, If, Ii, Ij, Im, Ir, Is or Iy are preferred here.

In the compounds of the formulae above and below, $R^1$, $R^2$ and $R^3$ are preferably alkyl or alkoxy.

Compounds of the formulae above and below in which one of the radicals $R^1$, $R^2$ and $R^3$ is CN, F or Cl are furthermore preferred.

$A^2$, $A^3$ and $A^4$ are preferably unsubstituted or mono- or polysubstituted 1,4-phenylene, 1,4-cyclohexylene, 1,3-dioxane-2,5-diyl or pyrimidine-2,5-diyl. In the case of substituted groups, monosubstitution is preferred. Possible substituents are F, Cl, CH$_3$ or CN. The preferred substituent is fluorine. p is preferably 1.

$Z^1$, $Z^2$ and $Z^3$ are preferably single bonds, and secondly preferably —CO—O— or —O—CH$_2$— and the corresponding inverted groups or —CH$_2$CH$_2$— groups. These ethylene groups can also be in substituted form and then preferably correspond to the group —CHR$^6$—CH$_2$—, wherein the substituent R$^6$ can be a halogen atom, a CN group or an alkyl group with up to 5 C atoms. R$^6$ is preferably F, Cl, CH$_3$ or CN.

If $R^1$ and/or $R^2$ or $R^3$ are alkyl radicals and/or alkoxy radicals, they can be straight-chain or branched. Preferably, they are straight-chain and have 2, 3, 4, 5, 6, or 7 C atoms, and accordingly are preferably ethyl, propyl, butyl, pentyl, hexyl, heptyl, ethoxy, propoxy, butoxy, pentoxy, hexoxy or heptoxy, or furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Compounds of the formulae I with branched wing groups $R^1$, $R^2$ and $R^3$ may occasionally be of importance because of a better solubility in the usual liquid crystal base materials, but in particular as chiral doping substances if they are optically active.

Branched groups of this type as a rule contain not more than one chain branching. Preferred branched radicals $R^1$, $R^2$ or $R^3$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl, 4-methylhexyl, 2-nonyl, 2-decyl, 2-dodecyl, 6-methyloctoxy, 6-methyloctanoyloxy, 5-methylheptyloxycarbonyl, 2-methylbutyryloxy, 3-methylvaleryloxy, 4-methylhexanoyloxy, 2-methyl-3-oxapentyl, 2-methyl-3-oxahexyl, 2-chloropropionyloxy, 2-chloro-3-methylbutyryloxy, 2-chloro-4-methylvaleryloxy and 2-chloro-3-methylvaleryloxy.

In the structural element A, X is CR$^4$ or N. Y is CHR$^4$, O, S or NR$^5$, preferably S, O or NR$^5$.

R$^5$ here is H, alkyl with 1-15 C atoms, halogen or cyano, preferably H or alkyl with 1-7 C atoms. R$^5$ is an H atom or an alkyl group with 1-15, preferably with 1-7, C atoms. Suitable alkyl groups are those described above.

If Y is CHR$^4$, X is N.

The substituent M can be a CN or NCS group, a halogen atom, an H atom or an alkyl group with 1-5 C atoms. M is preferably H, CN or an alkyl group. Of the halogen atoms F, Cl Br and I, F and Cl are preferred.

The following formulae (1) to (7) are preferred representatives of structural element A:

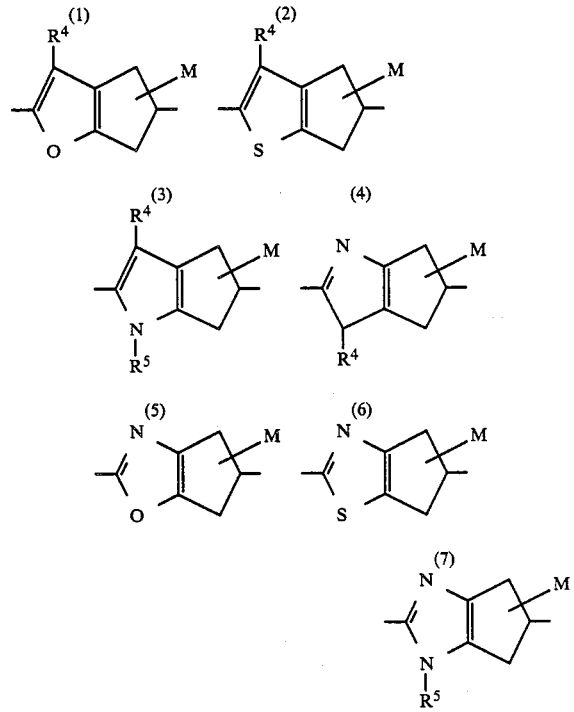

The structural elements (2) and (6) are particularly preferred.

M in the formulae (1)–(7) has the meaning given. M is preferably in the 5-position, but can also be in the 4- or 6-position.

The compounds of the formula I are prepared by methods which are known per se such as are described in the literature (for example in the standard works such as Houben-Weyl, Methoden der Organischen Chemie (Methods of Organic Chemistry), Georg-Thieme-Verlag, Stuttgart), and in particular under reaction conditions which are known and suitable for the reactions mentioned. It is also possible thereby to use variants which are known per se but are not mentioned here in more detail.

If desired, the starting substances can also be formed in situ, such that they are not isolated from the reaction mixture but are immediately reacted further to give the compounds of the formula I.

The compounds of the formula I can thus be prepared by reducing a compound which otherwise corresponds to the formula I but contains one or more reducible groups and/or C—C bonds instead of H atoms.

Preferred possible reducible groups are carbonyl groups, in particular keto groups, and furthermore, for example, free or esterified hydroxyl groups or aromatically bonded halogen atoms. Preferred starting substances for the reduction correspond to the formula I, but can also contain a cyclohexene ring or cyclohexanone ring instead of a cyclohexane rings and/or a —CH=CH— group instead of a —CH$_2$CH$_2$— group, and/or a —CO— group instead of a —CH$_2$— group, and/or a free or a functionally modified OH group (for example in the form of its p-toluenesulfonate) instead of an H atom.

The reduction can be carried out, for example, by catalytic hydrogenation at temperatures between about 0° and about 200° under pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Advantageously suitable catalysts are noble metals, such as Pt or Pd, which can be used in the form of oxides (for example $PtO_2$ and PdO) on a support (for example Pd-on-charcoal, calcium carbonate or strontium carbonate), or in finely divided form.

Ketones can also be reduced by the methods of Clemmensen (with zinc, zinc amalgam or tin and hydrochloric acid, advantageously in aqueous-alcoholic solution or in a heterogeneous phase system with water/toluene, at temperatures between about 80° and 120°) or Wolff-Kishner (with hydrazine, advantageously in the presence of an alkali, such as KOH or NaOH, in a highboiling solvent, such as diethylene glycol or triethylene glycol, at temperatures between about 100° and 200°), to give the corresponding compounds of the formula I containing alkyl groups and/or —$CH_2CH_2$— bridges.

Reductions with complex hydrides are furthermore possible. For example, arylsulfonyloxy groups can be removed by reduction with $LiAlH_4$, and in particular ptoluenesulfonyloxymethyl groups can be reduced to methyl groups, advantageously in an inert solvent, such as diethyl ether or THF, at temperatures between about 0° and 100°. Double bonds (even in the presence of CN groups!) can be hydrogenated with $NaBH_4$ or tributyltin hydride in methanol.

The structural elements A can be prepared in a particularly advantageous manner by cyclization of corresponding thiophene, furan or pyrrole compounds substituted by propionic acid derivatives in the 3-position. The cyclization here is carried out by methods which are known per se, for example by the corresponding acid chlorides or anhydrides or reactive esters, preferably in an inert solvent.

Another advantageous process for the preparation of the structural element A comprises cyclizing thiophene, thiazole, oxazole, pyrrole, furan or imidazole-2,3-dicarboxylic acid esters. The carbonyl groups are first reduced here. Cyclization to the cyclopentane ring is then carried out via the corresponding tosylate by reaction with a malonic ester by processes which are known per se.

Esters of the formula I can also be obtained by esterifying corresponding carboxylic acids (or their reactive derivatives) with alcohols or phenols (or their reactive derivatives).

Suitable reactive derivatives of the carboxylic acids mentioned are, in particular, the acid halides, above all the chlorides and bromides, and furthermore the anhydrides, for example also mixed anhydrides, azides or esters, in particular alkyl esters with 1-4 C atoms in the alkyl group.

Particularly suitable reactive derivatives of the alcohols or phenols mentioned are the corresponding metal alcoholates or phenolates, preferably of an alkali metal, such as Na or K.

The esterification is advantageously carried out in the presence of an inert solvent. Particularly suitable solvents are ethers, such as diethyl ether, di-n-butyl ether, THF, dioxane or anisole, ketones, such as acetone, butanone, or cyclohexanone, amides such as DMF or phosphoric acid hexamethyltriamide, hydrocarbons, such as benzene, toluene or xylene, halogenohydrocarbons, such as carbon tetrachloride or tetrochloroethylene, and sulfoxides, such as dimethyl sulfoxide or sulfolane. Waterimmiscible solvents can at the same time advantageously be used for azeotropic removal by distillation of the water formed during the esterification. An excess of an organic base, for example pyridine, quinoline or triethylamine, may occasionally also be used as the solvent for the esterification. The esterification can also be carried out in the absence of a solvent, for example by simply heating the components in the presence of sodium acetate. The reaction temperature is usually between −50° and +250°, preferably between −20° and +80°. At these temperatures, the esterification reactions are as a rule complete after 15 minutes to 48 hours.

In detail, the reaction conditions for the esterification depend largely on the nature of the starting substances used. Thus, a free carboxylic acid is as a rule reacted with a free alcohol or phenol in the presence of a strong acid, for example a mineral acid, such as hydrochloric acid or sulfuric acid. A preferred reaction procedure is to react an acid anhydride or, in particular, an acid chloride with an alcohol, preferably in a basic medium, bases which are of importance being, in particular, alkali methal hydroxides, such as sodium hydroxide or potassium hydroxide, alkali metal carbonates or bicarbonates, such as sodium carbonate, sodium bicarbonate, potassium carbonate or potassium bicarbonate, alkali metal acetates, such as sodium acetate or potassium acetate, alkaline earth metal hydroxides, such as calcium hydroxide, or organic bases, such as triethylamine, pyridine, tutidine, collidine or quinoline. Another preferred embodiment of the esterification comprises first converting the alcohol or phenol into the sodium alcoholate or phenolate or potassium alcoholate or phenolate, for example by treatment with ethanolic sodium hydroxide solution or potassium hydroxide solution, isolating this alcoholate or phenolate the suspending it in acetone or diethyl ether together with sodium bicarbonate or potassium carbonate, with stirring, and adding a solution of the acid chloride or anhydride in diethyl ether, acetone or DMF to this suspension, advantageously at temperatures between about −25° and +20°.

To prepare nitriles of the formula I (wherein $R^1$, $R^2$ or $R^3$ is CN and/or wherein $A^2$, $A^3$ and/or $A^4$ is substituted by at least one CN group), corresponding acid amides can be dehydrated. The amides are obtainable, for example, from corresponding esters or acid halides by reaction with ammonia. Examples of suitable dehydrating agents are inorganic acid chlorides, such as $SOCl_2$, $PCl_3$, $PCl_5$, $POCl_3$, $SO_2Cl_2$ or $COCl_2$, and furthermore $P_2O_5$, $P_2S_5$, $AlCl_3$ (for example as a double compound with NaCl), aromatic sulfonic acids and sulfonic acid halides. The reaction here can be carried out in the presence or absence of an inert solvent at temperatures between about 0° and 150°; possible solvents are, for example, bases, such as pyridine or triethylamine, aromatic hydrocarbons, such as benzene, toluene or xylene, or amides, such as DMF.

To prepare the abovementioned nitriles of the formula I, it is also possible to react corresponding acid halides, preferably the chlorides, with sulfamide, advantageously in an inert solvent, such as tetramethylene sulfone, at temperatures between about 80° and 150°, preferably at 120°. After customary working up, the nitriles can be isolated directly.

Ethers of the formula I (wherein $R^1$ and/or $R^2$ and/or $R^3$ is an alkoxy group and/or wherein $Z^1$ and/or $Z^2$ and/or $Z^3$ is a —OCH$_2$— or a —CH$_2$O—) group are obtainable by etherification of corresponding hydroxy compounds, preferably corresponding phenols, the hydroxy compound advantageously first being converted into a corresponding metal derivative, for example into the corresponding alkali metal alcoholate or alkali metal phenolate by treatment with NaH, NaNH$_2$, NaOH, KOH, Na$_2$CO$_3$ or K$_2$CO$_3$. This can then be reacted with the corresponding alkyl halide or -sulfonate or dialkyl sulfate, advantageously in an inert solvent, such as acetone, 1,2-dimethoxyethane, DMF or dimethyl sulfoxide, or an excess of aqueous or aqueous-alcoholic NaOH or KOH at temperatures between about 20° and 100°.

To prepare nitriles of the formula I (wherein $R^1$, $R^2$ and $R^3$ is CN and/or wherein $A^2$, $A^3$ and/or $A^4$ is substituted by at least one CN group), it is also possible for corresponding chlorine or bromine compounds of the formula I to be reacted with a cyanide, advantageously with a metal cyanide, such as NaCn, KCN or Cu$_2$(CN)$_2$, for example in the presence of pyridine in an inert solvent, such as DMF or N-methylpyrrolidone, at temperatures between 20° and 200°.

Compounds of the formua I wherein $R^1$ or $R^2$ or $R^3$ is F, Cl, Br or CN can also be obtained from the corresponding diazonium salts by replacement of the diazonium group by a fluorine, chlorine or bromine atom or by a CN group, for example by the methods of Schiemann or Sandmeyer.

The diazonium salts can be prepared, for example, by nitration of compounds which correspond to the formula I but contain one (or two) hydrogen atom(s) instead of the radicals $R^1$ or $R^2$ or $R^3$, reduction to the corresponding amines and diazotization, for example with NaNO$_2$ or KNO$_2$ in aqeuous solution at temperatures between about $-10°$ and $+10°$.

To replace the diazonium group by fluorine, the diazotization can be carried out in anhydrous hydrofluoric acid and the diazotization product can then be heated, or the reaction is carried out with tetrafluoboric acid to give the diazonium tetrafluoborates, which are then decomposed by heat.

Replacement by Cl, Br or CN is advantageously effected by reaction of the aqueous diazonium salt solution with Cu$_2$Cl$_2$, Cu$_2$Br$_2$ or Cu$_2$(CN)$_2$ by the method of Sandmeyer.

The liquid crystal phases according to the invention comprise 2 to 25, preferably 3 to 15, components, at least one of which is a liquid crystal compound containing the structural element A or a compound of the formula I. The other contituents are preferably selected from the nematic or nematogenic substances, in particular the known substances, from the classes of azoxybenzenes, benzylideneanilines, biphenyls, terphenyls, phenyl or cyclohexyl benzoates, phenyl or cyclohexyl cyclohexane-carboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenyl- or cyclohexylpyrimidines, phenyl- or cyclohexyldioxanes, phenyl- or cyclohexyldithianes, 1,2-bis-phenylethanes, 1,2-bis-cyclohexylethanes, 1-phenyl-2-cyclohexylethanes, optionally halogenated stilbenes, benzylphenyl ethers, tolanes and substituted cinnamic acids.

The most important compounds suitable as constituents of such liquid crystal phases can be characterized by the formula II $$R'—L—G—E—R''$$ II wherein L and E are each a carbo- or heterocyclic ring system from the group formed by 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-di-substituted naphthalene, di- and tetrahydronaphthalene, quinazoline and tetrahydroquinazoline, G is

| | |
|---|---|
| —CH=CH— | —N(O)=N— |
| —CH=CY— | —CH=N(O)— |
| —C≡C— | —CH$_2$—CH$_2$— |
| —CO—O— | —CH$_2$—O— |
| —CO—S— | —CH$_2$—S— |
| —CH=N— | —COO—Phe—COO— | or a C—C single bond, Y is halogen, preferably chlorine, or —CN and R' and R'' are alkyl, alkoxy, alkanoyloxy or alkoxycarbonyloxy with up to 18, preferably up to 8, carbon atoms, or one of these radicals is also CN, NC, NO$_2$, CF$_3$, F, Cl or Br.

In most of these compounds, R' and R'' differ from one another, one of these radicals usually being an alkyl or alkoxy group. However, other variants of the envisaged substituents are also customary. Many such substances or mixtures thereof are commercially available. All of these substances can be prepared by methods which are known from the literature.

The liquid crystal phases according to the invention contain about 0.1 to 99, preferably 10 to 95% of one or more compounds containing the structural element A or one or more compounds of the formula I. Liquid crystal phases which contain 0.1-50, in particular 0.5-30% of one or more compounds according to the invention are furthermore preferred.

Compounds of the formula I with an optically active wing group are suitable as components of nematic liquid crystal phases for avoiding reverse twist and for improving the elastic constants.

The optically active compounds of the formula I are moreover also suitable as components of chirally tilted smectic liquid crystal phases.

These phases contain in the achiral base mixture, as well as chiral compounds of the formula I, at least one other component with negative or relatively low positive dielelectric anisotropy.

Compounds containing the structural element A, B or C

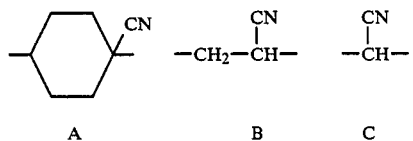

A   B   C are suitable as other components with negative dielectric anisotropy.

Preferred compounds of this type correspond to the formulae IV a, IV b and IV c:

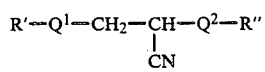

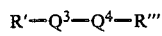

R' and R" are each preferably straight-chain alkyl or alkoxy groups with in each case 2 to 10 C atoms. $Q^1$ and $Q^2$ are each 1,4-phenylene, trans-1,4-cyclohexylene, 4,4'-biphenylyl, 4-(trans-4-cyclohexyl)-phenyl or trans,-trans-4,4'-bicyclohexyl, or one of the groups $Q^1$ and $Q^2$ is also a single bond.

$Q^3$ and $Q^4$ are each 1,4-phenylene, 4,4'-biphenylyl or trans-1,4-cyclohexylene. One of the groups $Q^3$ and $Q^4$ can also be 1,4-phenylene, wherein at least one CH group is replaced by N. R''' is an optically active radical with an asymmetric carbon atom of the structure

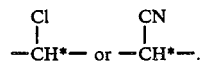

Particularly preferred compounds of the formula IV c are those of the formual IV c':

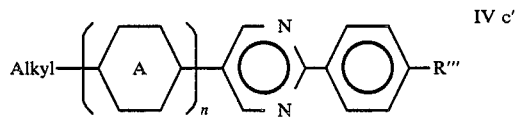

wherein A is 1,4-phenylene or trans-1,4-cyclohexylene and n is 0 or 1.

The dielectrics according to the invention are prepared in a manner which is customary per se. As a rule, the components are dissolved in one another, advantageously at elevated temperature.

The liquid crystal dielectrics according to the invention can be modified by suitable additives so that they can be used in all the types of liquid cyrstal display elements which have been disclosed to date. Such additives are known to the expert and are described in detail in the literature. For example, it is possible to add conductive salts, preferably ethyl-dimethyl-dodecylammonium 4-hexyloxybenzoate, tetrabutylammonium tetraphenylboranate or complex salts of crown ethers (compare, for example, I. Haller et al., Mol.Cryst.Liq.-Cryst. Volume 24, pages 249-258 (1973) to improve the conductivity, dichroic dyestuffs for the production of coloured guest-host systems or substances for modifying the dielectric anisotropy, the viscosity and/or the orientation of the nematic phases. Such substances are described, for example, in German Offenlegungsschriften No. 2,209,127, 2,240,854, 2,321,632, 2,338,281, 2,450,088, 2,637,430, 2,853,728 and 2,902,177.

The starting materials used in the reactions described above are all known or readily preparable from known starting materials using conventional methods.

Without further elaboration, it is believed that one skilled in the art can, using the preceding description, utilize the present invention to its fullest extend. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

m.p.=melting point, c.p.=clear point.

"Customary working up" means: water is added, the mixture is extracted with methylene chloride, the organic phase is separated off, dried and evaporated and the product is purified by crystallization and/or chromatography.

Where substitution is stated to be possible on rings, then up to 1 substituent per substitutable position is possible on each ring. Typically, there are 1-3 substituents on each ring. For dec and tet,typically there are 1 or 2 CN substituents. Moreover, throughout the foregoing and the following, "halogen" generically refers to all four possibilities, F, Cl, Br and I, F and Cl being preferred.

If any of $R^1$, $R^2$ and/or $R^3$ stands for an alkyl group wherein one or two $CH_2$ groups are replaced by any of —CHCN— and/or —CH=CH—, the groups $R^1$, $R^2$ and/or $R^3$ may contain up to 17 C atoms.

EXAMPLE 1

1.63 g of dicyclohexylcarbodiimide in 2.5 ml of methylene chloride are added to a mixture of 1.78 g of 5-n-pentyl-5,6-dihydro-4-H-cyclopenta[b]thiophene-2-carboxylic acid (which can be prepared from 3-bromomethylthiophene by reaction with n-heptanecarboxylic acid and lithium diisopropylamide, subsequent cyclization via the corresponding acid chloride, reduction of the carbonyl group (for example Wolff-Kishner reduction), Friedel-Crafts acetylation and a haloform reaction), 0.098 g of 4-dimethylaminopyridine, 1.42 g of 4-n-heptylphenol and 12 ml of methylene chloride at 10°, with stirring. After the mixture has been stirred at room temperature for 15 hours, it is filtered with suction over silica gel and the solvent is evaporated off. Recrystallization from ethanol gives 4-n-heptylphenyl 5-n-pentyl-5,6-dihydro-4-H-cyclopenta[b]thiophene-2-carboxylate of m.p. 64° and c.p. 82°.

The following compounds are prepared analogously:
4-n-heptylphenyl 5-methyl-5,6-dihydro-4-H-cyclopenta[b]thiophene-2-carboxylate
4-heptylphenyl 5-ethyl-5,6-dihydro-4-H-cyclopenta[b]thiophene-2-carboxylate
4-n-heptylphenyl 5-propyl-5,6-dihydro-4-H-cyclopenta[b]thiophene-2-carboxylate
4-n-heptylphenyl 5-butyl-5,6-dihydro-4-H-cyclopenta[b]thiophene-2-carboxylate
4-n-heptylphenyl 5-hexyl-5,6-dihydro-4-H-cyclopenta[b]thiophene-2-carboxylate
4-n-heptylphenyl 5-heptyl-5,6-dihydro-4-H-cyclopenta[b]thiophene-2-carboxylate
4-n-heptylphenyl 5-octyl-5,6-dihydro-4-H-cyclopenta[b]thiophene-2-carboxylate
4-hexylphenyl 5-methyl-5,6-dihydro-4-H-cyclopenta[b]thiophene-2-carboxylate
4-hexylphenyl 5-ethyl-5,6-dihydro-4-cyclopenta[b]thiophene-2-carboxylate
4-hexylphenyl 5-propyl-5,6-dihydro-4-H-cyclopenta[b]thiophene-2-carboxylate 4-hexylphenyl 5-butyl-5,6-dihydro-4-H-cyclopenta[b]thiophene-2-carboxylate
4-hexylphenyl 5-pentyl-5,6-dihydro-4-H-cyclopenta[b]thiophene-2-carboxylate
4-hexylphenyl 5-hexyl-5,6-dihydro-4-H-cyclopenta[b]thiophene-2-carboxylate
4-hexylphenyl 5-heptyl-5,6-dihydro-4-H-cyclopenta[b]thiophene-2-carboxylate
4-hexylphenyl 5-octyl-5,6-dihydro-4-H-cyclopenta[b]thiophene-2-carboxylate
4-pentylphenyl 5-methyl-5,6-dihydro-4-H-cyclopenta[b]thiophene-2-carboxylate
4-pentylphenyl 5-ethyl-5,6-dihydro-4-H-cyclopenta[b]thiophene-2-carboxylate
4-pentylphenyl 5-propyl-5,6-dihydro-4-H-cyclopenta[b]thiophene-2-carboxylate
4-pentylphenyl 5-butyl-5,6-dihydro-4-H-cyclopenta[b]thiophene-2-carboxylate
4-pentylphenyl 5-pentyl-5,6-dihydro-4-H-cyclopenta[b]thiophene-2-carboxylate
4-pentylphenyl 5-hexyl-5,6-dihydro-4-H-cyclopenta[b]thiophene-2-carboxylate
4-pentylphenyl 5-heptyl-5,6-dihydro-4-H-cyclopenta[b]thiophene-2-carboxylate
4-pentylphenyl 5-octyl-5,6-dihydro-4-H-cyclopenta[b]thiophene-2-carboxylate
4-butylphenyl 5-methyl-5,6-dihydro-4-H-cyclopenta[b]thiophene-2-carboxylate
4-butylphenyl 5-ethyl-5,6-dihydro-4-H-cyclopenta[b]thiophene-2-carboxylate
4-butylphenyl 5-propyl-5,6-dihydro-4-H-cyclopenta[b]thiophene-2-carboxylate
4-butylphenyl 5-butyl-5,6-dihydro-4-H-cyclopenta[b]thiophene-2- carboxylate
4-butylphenyl 5-pentyl-5,6-dihydro-4-H-cyclopenta[b]thiophene-2-carboxylate
4-butylphenyl 5-hexyl-5,6-dihydro-4-H-cyclopenta[b]thiophene-2-carboxylate
4-butylphenyl 5-heptyl-5,6-dihydro-4-H-cyclopenta[b]thiophene-2-carboxylate
4-butylphenyl 5-octyl-5,6-dihydro-4-H-cyclopenta[b]thiophene-2-carboxylate
4-propylphenyl 5-methyl-5,6-dihydro-4-H-cyclopenta[b]thiophene-2-carboxylate
4-propylphenyl 5-ethyl-5,6-dihydro-4-H-cyclopenta[b]thiophene-2-carboxylate
4-propylphenyl 5-propyl-5,6-dihydro-4-H-cyclopenta[b]thiophene-2-carboxylate
4-propylphenyl 5-butyl-5,6-dihydro-4-H-cyclopenta[b]thiophene-2-carboxylate
4-propylphenyl 5-pentyl-5,6-dihydro-4-H-cyclopenta[b]thiophene-2-carboxylate
4-propylphenyl 5-hexyl-5,6-dihydro-4-H-cyclopenta[b]thiophene-2-carboxylate
4-propylphenyl 5-heptyl-5,6-dihydro-4-H-cyclopenta[b]thiophene-2-carboxylate
4-propylphenyl 5-octyl-5,6-dihydro-4-H-cyclopenta[b]thiophene-2-carboxylate
4-isopropylphenyl 5-methyl-5,6-dihydro-4-H-cyclopenta[b]thiophene-2-carboxylate
4-isopropylphenyl 5-ethyl-5,6-dihydro-4-H-cyclopenta[b]thiophene-2-carboxylate
4-isopropylphenyl 5-propyl-5,6-dihydro-4-H-cyclopenta[b]thiophene-2-carboxylate
4-isopropylphenyl 5-butyl-5,6-dihydro-4-H-cyclopenta[b]thiophene-2-carboxylate
4-isopropylphenyl 5-pentyl-5,6-dihydro-4-H-cyclopenta[b]thiophene-2-carboxylate
4-isopropylphenyl 5-hexyl-5,6-dihydro-4-H-cyclopenta[b]thiophene-2-carboxylate
4-isopropylphenyl 5-heptyl-5,6-dihydro-4-H-cyclopenta[b]thiophene-2-carboxylate
4-isopropylphenyl 5-octyl-5,6-dihydro-4-H-cyclopenta[b]thiophene-2-carboxylate
4-butyloxyphenyl 5-methyl-5,6-dihydro-4-H-cyclopenta[b]thiophene-2-carboxylate
4-butyloxyphenyl 5-ethyl-5,6-dihydro-4-H-cyclopenta[b]thiophene-2-carboxylate
4-butyloxyphenyl 5-propyl-5,6-dihydro-4-H-cyclopenta[b]thiophene-2-carboxylate
4-butyloxyphenyl 5-butyl-5,6-dihydro-4-H-cyclopenta[b]thiophene-2-carboxylate
4-butyloxyphenyl 5-pentyl-5,6-dihydro-4-H-cyclopenta[b]thiophene-2-carboxylate
4-butyloxyphenyl 5-hexyl-5,6-dihydro-4-H-cyclopenta[b]thiophene-2-carboxylate
4-butyloxyphenyl 5-heptyl-5,6-dihydro-4-H-cyclopenta[b]thiophene-2-carboxylate
4-butyloxyphenyl 5-octyl-5,6-dihydro-4-H-cyclopenta[b]thiophene-2-carboxylate
4-pentyloxyphenyl 5-methyl-5,6-dihydro-4-H-cyclopenta[b]thiophene-2-carboxylate
4-pentyloxyphenyl 5-ethyl-5,6-dihydro-4-H-cyclopenta[b]thiophene-2-carboxylate
4-pentyloxyphenyl 5-propyl-5,6-dihydro-4-H-cyclopenta[b]thiophene-2-carboxylate
4-pentyloxyphenyl 5-butyl-5,6-dihydro-4-H-cyclopenta[b]thiophene-2-carboxylate
4-pentyloxyphenyl 5-pentyl-5,6-dihydro-4-H-cyclopenta[b]thiophene-2-carboxylate
4-pentyloxyphenyl 5-hexyl-5,6-dihydro-4-H-cyclopenta[b]thiophene-2-carboxylate
4-pentyloxyphenyl 5-heptyl-5,6-dihydro-4-H-cyclopenta[b]thiophene-2-carboxylate
4-pentyloxyphenyl 5-octyl-5,6-dihydro-4-H-cyclopenta[b]thiophene-2-carboxylate
4-hexyloxyphenyl 5-methyl-5,6-dihydro-4-H-cyclopenta[b]thiophene-2-carboxylate
4-hexyloxyphenyl 5-ethyl-5,6-dihydro-4-H-cyclopenta[b]thiophene-2-carboxylate
4-hexyloxyphenyl 5-propyl-5,6-dihydro-4-H-cyclopenta[b]thiophene-2-carboxylate
4-hexyloxyphenyl 5-butyl-5,6-dihydro-4-H-cyclopenta[b]thiophene-2-carboxylate
4-hexyloxyphenyl 5-pentyl-5,6-dihydro-4-H-cyclopenta[b]thiophene-2-carboxylate
4-hexyloxyphenyl 5-hexyl-5,6-dihydro-4-H-cyclopenta[b]thiophene-2-carboxylate
4-hexyloxyphenyl 5-heptyl-5,6-dihydro-4-H-cyclopenta[b]thiophene-2-carboxylate
4-hexyloxyphenyl 5-octyl-5,6-dihydro-4-H-cyclopenta[b]thiophene-2-carboxylate
4-heptyloxyphenyl 5-methyl-5,6-dihydro-4-H-cyclopenta[b]thiophene-2-carboxylate
4-heptyloxyphenyl 5-ethyl-5,6-dihydro-4-H-cyclopenta[b]thiophene-2-carboxylate
4-heptyloxyphenyl 5-propyl-5,6-dihydro-4-H-cyclopenta[b]thiophene-2-carboxylate
4-heptyloxyphenyl 5-butyl-5,6-dihydro-4-H-cyclopenta[b]thiophene-2-carboxylate
4-heptyloxyphenyl 5-pentyl-5,6-dihydro-4-H-cyclopenta[b]thiophene-2-carboxylate
4-heptyloxyphenyl 5-hexyl-5,6-dihydro-4-H-cyclopenta[b]thiophene-2-carboxylate
4-heptyloxyphenyl 5-heptyl-5,6-dihydro-4-H-cyclopenta[b]thiophene-2-carboxylate 4-heptyloxyphenyl 5-octyl-5,6-dihydro-4-H-cyclopenta[b]thiophene-2-carboxylate
4-heptylphenyl 5-methyl-5,6-dihydro-4-H-cyclopenta[b]furan-2-carboxylate
4-heptylphenyl 5-ethyl-5,6-dihydro-4-H-cyclopenta[b]furan-2-carboxylate
4-heptylphenyl 5-propyl-5,6-dihydro-4-H-cyclopenta[b]furan-2-carboxylate
4-heptylphenyl 5-butyl-5,6-dihydro-4-H-cyclopenta[b]furan-2-carboxylate
4-heptylphenyl 5-pentyl-5,6-dihydro-4-H-cyclopenta[b]furan-2-carboxylate
4-heptylphenyl 5-hexyl-5,6-dihydro-4-H-cyclopenta[b]furan-2-carboxylate
4-heptylphenyl 5-heptyl-5,6-dihydro-4-H-cyclopenta[b]furan-2-carboxylate
4-heptylphenyl 5-octyl-5,6-dihydro-4-H-cyclopenta[b]furan-2-carboxylate
4-hexylphenyl 5-methyl-5,6-dihydro-4-H-cyclopenta[b]furan-2-carboxylate
4-hexylphenyl 5-ethyl-5,6-dihydro-4-H-cyclopenta[b]furan-2-carboxylate
4-hexylphenyl 5-propyl-5,6-dihydro-4-H-cyclopenta[b]furan-2-carboxylate
4-hexylphenyl 5-butyl-5,6-dihydro-4-H-cyclopenta[b]furan-2-carboxylate
4-hexylphenyl 5-pentyl-5,6-dihydro-4-H-cyclopenta[b]furan-2-carboxylate
4-hexylphenyl 5-hexyl-5,6-dihydro-4-H-cyclopenta[b]furan-2-carboxylate
4-hexylphenyl 5-heptyl-5,6-dihydro-4-H-cyclopenta[b]furan-2-carboxylate
4-hexylphenyl 5-octyl-5,6-dihydro-4-H-cyclopenta[b]furan-2-carboxylate
4-pentylphenyl 5-methyl-5,6-dihydro-4-H-cyclopenta[b]furan-2-carboxylate
4-pentylphenyl 5-ethyl-5,6-dihydro-4-H-cyclopenta[b]furan-2-carboxylate
4-pentylphenyl 5-propyl-5,6-dihydro-4-H-cyclopenta[b]furan-2-carboxylate
4-pentylphenyl 5-butyl-5,6-dihydro-4-H-cyclopenta[b]furan-2-carboxylate
4-pentylphenyl 5-pentyl-5,6-dihydro-4-H-cyclopenta[b]furan-2-carboxylate
4-pentylphenyl 5-hexyl-5,6-dihydro-4-H-cyclopenta[b]furan-2-carboxylate
4-pentylphenyl 5-heptyl-5,6-dihydro-4-H-cyclopenta[b]furan-2-carboxylate
4-pentylphenyl 5-octyl-5,6-dihydro-4-H-cyclopenta[b]furan-2-carboxylate
4-butylphenyl 5-methyl-5,6-dihydro-4-H-cyclopenta[b]furan-2-carboxylate
4-butylphenyl 5-ethyl-5,6-dihydro-4-H-cyclopenta[b]furan-2-carboxylate
4-butylphenyl 5-propyl-5,6-dihydro-4-H-cyclopenta[b]furan-2-carboxylate
4-butylphenyl 5-butyl-5,6-dihydro-4-H-cyclopenta[b]furan-2-carboxylate
4-butylphenyl 5-pentyl-5,6-dihydro-4-H-cyclopenta[b]furan-2-carboxylate
4-butylphenyl 5-hexyl-5,6-dihydro-4-H-cyclopenta[b]furan-2-carboxylate
4-butylphenyl 5-heptyl-5,6-dihydro-4-H-cyclopenta[b]furan-2-carboxylate
4-butylphenyl 5-octyl-5,6-dihydro-4-H-cyclopenta[b]furan-2-carboxylate
4-propylphenyl 5-methyl-5,6-dihydro-4-H-cyclopenta[b]furan-2-carboxylate
4-propylphenyl 5-ethyl-5,6-dihydro-4-H-cyclopenta[b]furan-2-carboxylate
4-propylphenyl 5-propyl-5,6-dihydro-4-H-cyclopenta[b]furan-2-carboxylate
4-propylphenyl 5-butyl-5,6-dihydro-4-H-cyclopenta[b]furan-2-carboxylate
4-propylphenyl 5-pentyl-5,6-dihydro-4-H-cyclopenta[b]furan-2-carboxylate
4-propylphenyl 5-hexyl-5,6-dihydro-4-H-cyclopenta[b]furan-2-carboxylate
4-propylphenyl 5-heptyl-5,6-dihydro-4-H-cyclopenta[b]furan-2-carboxylate
4-propylphenyl 5-octyl-5,6-dihydro-4-H-cyclopenta[b]furan-2-carboxylate
4-isobutylphenyl 5-methyl-5,6-dihydro-4-H-cyclopenta[b]furan-2-carboxylate
4-isobutylphenyl 5-ethyl-5,6-dihydro-4-H-cyclopenta[b]furan-2-carboxylate
4-isobutylphenyl 5-propyl-5,6-dihydro-4-H-cyclopenta[b]furan-2-carboxylate
4-isobutylphenyl 5-butyl-5,6-dihydro-4-H-cyclopenta[b]furan-2-carboxylate
4-isobutylphenyl 5-pentyl-5,6-dihydro-4-H-cyclopenta[b]furan-2-carboxylate
4-isobutylphenyl 5-hexyl-5,6-dihydro-4-H-cyclopenta[b]furan-2-carboxylate
4-isobutylphenyl 5-heptyl-5,6-dihydro-4-H-cyclopenta[b]furan-2-carboxylate
4-isobutylphenyl 5-octyl-5,6-dihydro-4-H-cyclopenta[b]furan-2-carboxylate
4-pentyloxyphenyl 5-methyl-5,6-dihydro-4-H-cyclopenta[b]furan-2-carboxylate
4-pentyloxyphenyl 5-ethyl-5,6-dihydro-4-H-cyclopenta[b]furan-2-carboxylate
4-pentyloxyphenyl 5-propyl-5,6-dihydro-4-H-cyclopenta[b]furan-2-carboxylate
4-pentyloxyphenyl 5-butyl-5,6-dihydro-4-H-cyclopenta[b]furan-2-carboxylate
4-pentyloxyphenyl 5-pentyl-5,6-dihydro-4-H-cyclopenta[b]furan-2-carboxylate
4-pentyloxyphenyl 5-hexyl-5,6-dihydro-4-H-cyclopenta[b]furan-2-carboxylate
4-pentyloxyphenyl 5-heptyl-5,6-dihydro-4-H-cyclopenta[b]furan-2-carboxylate
4-pentyloxyphenyl 5-octyl-5,6-dihydro-4-H-cyclopenta[b]furan-2-carboxylate
4-hexyloxyphenyl 5-methyl-5,6-dihydro-4-H-cyclopenta[b]furan-2-carboxylate
4-hexyloxyphenyl 5-ethyl-5,6-dihydro-4-H-cyclopenta[b]furan-2-carboxylate
4-hexyloxyphenyl 5-propyl-5,6-dihydro-4-H-cyclopenta[b]furan-2-carboxylate
4-hexyloxyphenyl 5-butyl-5,6-dihydro-4-H-cyclopenta[b]furan-2-carboxylate
4-hexyloxyphenyl 5-pentyl-5,6-dihydro-4-H-cyclopenta[b]furan-2-carboxylate
4-hexyloxyphenyl 5-hexyl-5,6-dihydro-4-H-cyclopenta[b]furan-2-carboxylate
4-hexyloxyphenyl 5-heptyl-5,6-dihydro-4-H-cyclopenta[b]furan-2-carboxylate
4-hexyloxyphenyl 5-octyl-5,6-dihydro-4-H-cyclopenta[b]furan-2-carboxylate
4-butyloxyphenyl 5-methyl-5,6-dihydro-4-H-cyclopenta[b]furan-2-carboxylate
4-butyloxyphenyl 5-ethyl-5,6-dihydro-4-H-cyclopenta[b]furan-2-carboxylate
4-butyloxyphenyl 5-propyl-5,6-dihydro-4-H-cyclopenta[b]furan-2-carboxylate 4-butyloxyphenyl 5-butyl-5,6-dihydro-4-H-cyclopenta[b]furan-2-carboxylate
4-butyloxyphenyl 5-pentyl-5,6-dihydro-4-H-cyclopenta[b]furan-2-carboxylate
4-butyloxyphenyl 5-hexyl-5,6-dihydro-4-H-cyclopenta[b]furan-2-carboxylate
4-butyloxyphenyl 5-heptyl-5,6-dihydro-4-H-cyclopenta[b]furan-2-carboxylate
4-butyloxyphenyl 5-octyl-5,6-dihydro-4-H-cyclopenta[b]furan-2-carboxylate
4-heptylphenyl 5-methyl-5,6-dihydro-4-H-cyclopenta[b]pyrrole-2-carboxylate
4-heptylphenyl 5-ethyl-5,6-dihydro-4-H-cyclopenta[b]pyrrole-2-carboxylate
4-heptylphenyl 5-propyl-5,6-dihydro-4-H-cyclopenta[b]pyrrole-2-carboxylate
4-heptylphenyl 5-butyl-5,6-dihydro-4-H-cyclopenta[b]pyrrole-2-carboxylate
4-heptylphenyl 5-pentyl-5,6-dihydro-4-H-cyclopenta[b]pyrrole-2-carboxylate
4-heptylphenyl 5-hexyl-5,6-dihydro-4-H-cyclopenta[b]pyrrole-2-carboxylate
4-heptylphenyl 5-heptyl-5,6-dihydro-4-H-cyclopenta[b]pyrrole-2-carboxylate
4-heptylphenyl 5-octyl-5,6-dihydro-4-H-cyclopenta[b]pyrrole-2-carboxylate
4-hexylphenyl 5-methyl-5,6-dihydro-4-cyclopenta[b]pyrrole-2-carboxylate
4-hexylphenyl 5-ethyl-5,6-dihydro-4-H-cyclopenta[b]pyrrole-2-carboxylate
4-hexylphenyl 5-propyl-5,6-dihydro-4-H-cyclopenta[b]pyrrole-2-carboxylate
4-hexylphenyl 5-butyl-5,6-dihydro-4-H-cyclopenta[b]pyrrole-2-carboxylate
4-hexylphenyl 5-pentyl-5,6-dihydro-4-H-cyclopenta[b]pyrrole-2-carboxylate
4-hexylphenyl 5-hexyl-5,6-dihydro-4-H-cyclopenta[b]pyrrole-2-carboxylate
4-hexylphenyl 5-heptyl-5,6-dihydro-4-H-cyclopenta[b]pyrrole-2-carboxylate
4-hexylphenyl 5-octyl-5,6-dihydro-4-H-cyclopenta[b]pyrrole-2-carboxylate
4-pentylphenyl 5-methyl-5,6-dihydro-4-H-cyclopenta[b]pyrrole-2-carboxylate
4-pentylphenyl 5-ethyl-5,6-dihydro-4-H-cyclopenta[b]pyrrole-2-carboxylate
4-pentylphenyl 5-propyl-5,6-dihydro-4-H-cyclopenta[b]pyrrole-2-carboxylate
4-pentylphenyl 5-butyl-5,6-dihydro-4-H-cyclopenta[b]pyrrole-2-carboxylate
4-pentylphenyl 5-pentyl-5,6-dihydro-4-H-cyclopenta[b]pyrrole-2-carboxylate
4-pentylphenyl 5-hexyl-5,6-dihydro-4-H-cyclopenta[b]pyrrole-2-carboxylate
4-pentylphenyl 5-heptyl-5,6-dihydro-4-H-cyclopenta[b]pyrrole-2-carboxylate
4-pentylphenyl 5-octyl-5,6-dihydro-4-H-cyclopenta[b]pyrrole-2-carboxylate
4-butylphenyl 5-methyl-5,6-dihydro-4-H-cyclopenta[b]pyrrole-2-carboxylate
4-butylphenyl 5-ethyl-5,6-dihydro-4-H-cyclopenta[b]pyrrole-2-carboxylate
4-butylphenyl 5-propyl-5,6-dihydro-4-H-cyclopenta[b]pyrrole-2-carboxylate
4-butylphenyl 5-butyl-5,6-dihydro-4-H-cyclopenta[b]pyrrole-2-carboxylate
4-butylphenyl 5-pentyl-5,6-dihydro-4-H-cyclopenta[b]pyrrole-2-carboxylate
4-butylphenyl 5-hexyl-5,6-dihydro-4-H-cyclopenta[b]pyrrole-2-carboxylate
4-butylphenyl 5-heptyl-5,6-dihydro-4-H-cyclopenta[b]pyrrole-2-carboxylate
4-butylphenyl 5-octyl-5,6-dihydro-4-H-cyclopenta[b]pyrrole-2-carboxylate
4-propylphenyl 5-methyl-5,6-dihydro-4-H-cyclopenta[b]pyrrole-2-carboxylate
4-propylphenyl 5-ethyl-5,6-dihydro-4-H-cyclopenta[b]pyrrole-2-carboxylate
4-propylphenyl 5-propyl-5,6-dihydro-4-H-cyclopenta[b]pyrrole-2-carboxylate
4-propylphenyl 5-butyl-5,6-dihydro-4-H-cyclopenta[b]pyrrole-2-carboxylate
4-propylphenyl 5-pentyl-5,6-dihydro-4-H-cyclopenta[b]pyrrole-2-carboxylate
4-propylphenyl 5-hexyl-5,6-dihydro-4-H-cyclopenta[b]pyrrole-2-carboxylate
4-propylphenyl 5-heptyl-5,6-dihydro-4-H-cyclopenta[b]pyrrole-2-carboxylate
4-propylphenyl 5-octyl-5,6-dihydro-4-H-cyclopenta[b]pyrrole-2-carboxylate
4-ethylphenyl 5-methyl-5,6-dihydro-4-H-cyclopenta[b]pyrrole-2-carboxylate
4-ethylphenyl 5-ethyl-5,6-dihydro-4-H-cyclopenta[b]pyrrole-2-carboxylate
4-ethylphenyl 5-propyl-5,6-dihydro-4-H-cyclopenta[b]pyrrole-2-carboxylate
4-ethylphenyl 5-butyl-5,6-dihydro-4-H-cyclopenta[b]pyrrole-2-carboxylate
4-ethylphenyl 5-pentyl-5,6-dihydro-4-H-cyclopenta[b]pyrrole-2-carboxylate
4-ethylphenyl 5-hexyl-5,6-dihydro-4-H-cyclopenta[b]pyrrole-2-carboxylate
4-ethylphenyl 5-heptyl-5,6-dihydro-4-H-cyclopenta[b]pyrrole-2-carboxylate
4-ethylphenyl 5-octyl-5,6-dihydro-4-H-cyclopenta[b]pyrrole-2-carboxylate
4-pentyloxyphenyl 5-methyl-5,6-dihydro-4-H-cyclopenta[b]pyrrole-2-carboxylate
4-pentyloxyphenyl 5-ethyl-5,6-dihydro-4-H-cyclopenta[b]pyrrole-2-carboxylate
4-pentyloxyphenyl 5-propyl-5,6-dihydro-4-H-cyclopenta[b]pyrrole-2-carboxylate
4-pentyloxyphenyl 5-butyl-5,6-dihydro-4-H-cyclopenta[b]pyrrole-2-carboxylate
4-pentyloxyphenyl 5-pentyl-5,6-dihydro-4-H-cyclopenta[b]pyrrole-2-carboxylate
4-pentyloxyphenyl 5-hexyl-5,6-dihydro-4-H-cyclopenta[b]pyrrole-2-carboxylate
4-pentyloxyphenyl 5-heptyl-5,6-dihydro-4-H-cyclopenta[b]pyrrole-2-carboxylate
4-pentyloxyphenyl 5-octyl-5,6-dihydro-4-H-cyclopenta[b]pyrrole-2-carboxylate
4-hexyloxyphenyl 5-methyl-5,6-dihydro-4-H-cyclopental[b]pyrrole-2-carboxylate
4-hexyloxyphenyl 5-ethyl-5,6-dihydro-4-H-cyclopental[b]pyrrole-2-carboxylate
4-hexyloxyphenyl 5-propyl-5,6-dihydro-4-H-cyclopenta[b]pyrrole-2-carboxylate
4-hexyloxyphenyl 5-butyl-5,6-dihydro-4-H-cyclopenta[b]pyrrole-2-carboxylate
4-hexyloxyphenyl 5-pentyl-5,6-dihydro-4-H-cyclopenta[b]pyrrole-2-carboxylate
4-hexyloxyphenyl 5-hexyl-5,6-dihydro-4-H-cyclopenta[b]pyrrole-2-carboxylate
4-hexyloxyphenyl 5-heptyl-5,6-dihydro-4-H-cyclopenta[b]pyrrole-2-carboxylate 4-hexyloxyphenyl 5-octyl-5,6-dihydro-4-H-cyclopenta[b]pyrrole-2-carboxylate
4-heptyloxyphenyl 5-methyl-5,6-dihydro-4-H-cyclopenta[b]pyrrole-2-carboxylate
4-heptyloxyphenyl 5-ethyl-5,6-dihydro-4-H-cyclopenta[b]pyrrole-2-carboxylate
4-heptyloxyphenyl 5-propyl-5,6-dihydro-4-H-cyclopenta[b]pyrrole-2-carboxylate
4-heptyloxyphenyl 5-butyl-5,6-dihydro-4-H-cyclopenta[b]pyrrole-2-carboxylate
4-heptyloxyphenyl 5-pentyl-5,6-dihydro-4-H-cyclopenta[b]pyrrole-2-carboxylate
4-heptyloxyphenyl 5-hexyl-5,6-dihydro-4-H-cyclopenta[b]pyrrole-2-carboxylate
4-heptyloxyphenyl 5-heptyl-5,6-dihydro-4-H-cyclopenta[b]pyrrole-2-carboxylate
4-heptyloxyphenyl 5-octyl-5,6-dihydro-4-H-cyclopenta[b]pyrrole-2-carboxylate

EXAMPLE 2

Analogously to Example 1, 3-fluoro-4-cyanophenyl 5-n-pentyl-5,6-dihydro-4-H-cyclopenta[b]thiophene-2-carboxylate of m.p. 49° and c.p. 93° is obtained from 5-n-pentyl-5,6-dihydro-4-H-cyclopenta[b]thiophene-2-carboxylic acid by reaction with 3-fluoro-4-cyanophenol.

The following compounds are prepared analogously:
3-fluoro-4-cyanophenyl 5-methyl-5,6-dihydro-4-H-cyclopenta[b]thiophene-2-carboxylate
3-fluoro-4-cyanophenyl 5-ethyl-5,6-dihydro-4-H-cyclopenta[b]thiophene-2-carboxylate
3-fluoro-4-cyanophenyl 5-propyl-5,6-dihydro-4-H-cyclopenta[b]thiophene-2-carboxylate
3-fluoro-4-cyanophenyl 5-butyl-5,6-dihydro-4-H-cyclopenta[b]thiophene-2-carboxylate
3-fluoro-4-cyanophenyl 5-hexyl-5,6-dihydro-4-H-cyclopenta[b]thiophene-2-carboxylate
3-fluoro-4-cyanophenyl 5-heptyl-5,6-dihydro-4-H-cyclopenta[b]thiophene-2-carboxylate
3-fluoro-4-cyanophenyl 5-octyl-5,6-dihydro-4-H-cyclopenta[b]thiophene-2-carboxylate
3-fluoro-4-cyanophenyl 5-methyl-5,6-dihydro-4-H-cyclopenta[b]furan-2-carboxylate
3-fluoro-4-cyanophenyl 5-ethyl-5,6-dihydro-4-H-cyclopenta[b]furan-2-carboxylate
3-fluoro-4-cyanophenyl 5-propyl-5,6-dihydro-4-H-cyclopenta[b]furan-2-carboxylate
3-fluoro-4-cyanophenyl 5-butyl-5,6-dihydro-4-H-cyclopenta[b]furan-2-carboxylate
3-fluoro-4-cyanophenyl 5-pentyl-5,6-dihydro-4-H-cyclopenta[b]furan-2-carboxylate
3-fluoro-4-cyanophenyl 5-hexyl-5,6-dihydro-4-H-cyclopenta[b]furan-2-carboxylate
3-fluoro-4-cyanophenyl 5-heptyl-5,6-dihydro-4-H-cyclopenta[b]furan-2-carboxylate
3-fluoro-4-cyanophenyl 5-octyl-5,6-dihydro-4-H-cyclopenta[b]furan-2-carboxylate
3-fluoro-4-cyanophenyl 5-methyl-5,6-dihydro-4-H-cyclopenta[b]pyrrole-2-carboxylate
3-fluoro-4-cyanophenyl 5-ethyl-5,6-dihydro-4-H-cyclopenta[b]pyrrole-2-carboxylate
3-fluoro-4-cyanophenyl 5-propyl-5,6-dihydro-4-H-cyclopenta[b]pyrrole-2-carboxylate
3-fluoro-4-cyanophenyl 5-butyl-5,6-dihydro-4-H-cyclopenta[b]pyrrole-2-carboxylate
3-fluoro-4-cyanophenyl 5-pentyl-5,6-dihydro-4-H-cyclopenta[b]pyrrole-2-carboxylate
3-fluoro-4-cyanophenyl 5-hexyl-5,6-dihydro-4-H-cyclopenta[b]pyrrole-2-carboxylate
3-fluoro-4-cyanophenyl 5-heptyl-5,6-dihydro-4-H-cyclopenta[b]pyrrole-2-carboxylate
3-fluoro-4-cyanophenyl 5-octyl-5,6-dihydro-4-H-cyclopenta[b]pyrrole-2-carboxylate

EXAMPLE 3

6.1 ml of a 15% solution of butyllithium in hexane are added to a mixture of 1.4 ml of diisopropylamine in 10 ml of THF at −20°. 3.3 of g of 2-(4-n-hexyloxyphenyl)-5-cyano-5,6-dihydro-4-H-cyclopenta[d]thiazole (which can be prepared from ethyl 2-(4-n-hexyloxyphenyl)-thiazole-2,3-dicarboxylate by (a) reduction of the carbonyl groups, (b) conversion into the tosylate, (c) cyclization by reaction with diethyl malonate, (d) saponification and decarboxylation and (e) introduction of the nitrile group) in 10 ml of THF are then added at −60°, the mixture is stirred for 15 minutes, 1.8 g of 1-bromoheptane are then added and the mixture is stirred at −60° for a further 30 minutes and stirred overnight at room temperature. 10% ammonium chloride solution is added and the mixture is then worked up in the customary manner to give 2-(4-n-hexyloxyphenyl)-5-cyano-5-n-heptyl-5,6-dihydro-4-H-cyclopenta[d]thiazole.

The following compounds are prepared analogously:
2-(4-hexyloxyphenyl)-5-cyano-5-ethyl-5,6-dihydro-4-H-cyclopenta[d]thiazole
2-(4-hexyloxyphenyl)-5-cyano-5-propyl-5,6-dihydro-4-H-cyclopenta[d]thiazole
2-(4-hexyloxyphenyl)-5-cyano-5-butyl-5,6-dihydro-4-H-cyclopenta[d]thiazole
2-(4-hexyloxyphenyl)-5-cyano-5-pentyl-5,6-dihydro-4-H-cyclopenta[d]thiazole
2-(4-hexyloxyphenyl)-5-cyano-5-hexyl-5,6-dihydro-4-H-cyclopenta[d]thiazole
2-(4-hexyloxyphenyl)-5-cyano-5-octyl-5,6-dihydro-4-H-cyclopenta[d]thiazole
2-(4-pentyloxyphenyl)-5-cyano-5-ethyl-5,6-dihydro-4-H-cyclopenta[d]thiazole
2-(4-pentyloxyphenyl)-5-cyano-5-propyl-5,6-dihydro-4-H-cyclopenta[d]thiazole
2-(4-pentyloxyphenyl)-5-cyano-5-butyl-5,6-dihydro-4-H-cyclopenta[d]thiazole
2-(4-pentyloxyphenyl)-5-cyano-5-pentyl-5,6-dihydro-4-H-cyclopenta[d]thiazole
2-(4-pentyloxyphenyl)-5-cyano-5-hexyl-5,6-dihydro-4-H-cyclopenta[d]thiazole
2-(4-pentyloxyphenyl)-5-cyano-5-heptyl-5,6-dihydro-4-H-cyclopenta[d]thiazole
2-(4-pentyloxyphenyl)-5-cyano-5-octyl-5,6-dihydro-4-H-cyclopenta[d]thiazole
2-(4-butyloxyphenyl)-5-cyano-5-ethyl-5,6-dihydro-4-H-cyclopenta[d]thiazole
2-(4-butyloxyphenyl)-5-cyano-5-propyl-5,6-dihydro-4-H-Ocyclopenta[d]thiazole
2-(4-butyloxyphenyl)-5-cyano-5-butyl-5,6-dihydro-4-H-cyclopenta[d]thiazole
2-(4-butyloxyphenyl)-5-cyano-5-pentyl-5,6-dihydro-4-H-cyclopenta[d]thiazole
2-(4-butyloxyphenyl)-5-cyano-5-hexyl-5,6-dihydro-4-H-cyclopenta[d]thiazole
2-(4-butyloxyphenyl)-5-cyano-5-heptyl-5,6-dihydro-4-H-cyclopenta[d]thiazole
2-(4-butyloxyphenyl)-5-cyano-5-octyl-5,6-dihydro-4-H-cyclopenta[d]thiazole
2-(4-heptyloxyphenyl)-5-cyano-5-ethyl-5,6-dihydro-4-H-cyclopenta[d]thiazole 2-(4-heptyloxyphenyl)-5-cyano-5-propyl-5,6-dihydro-4-H-cyclopenta[d]thiazole
2-(4-heptyloxyphenyl)-5-cyano-5-butyl-5,6-dihydro-4-H-cyclopenta[d]thiazole
2-(4-heptyloxyphenyl)-5-cyano-5-pentyl-5,6-dihydro-4-H-cyclopenta[d]thiazole
2-(4-heptyloxyphenyl)-5-cyano-5-hexyl-5,6-dihydro-4-H-cyclopenta[d]thiazole
2-(4-heptyloxyphenyl)-5-cyano-5-heptyl-5,6-dihydro-4-H-cyclopenta[d]thiazole
2-(4-heptyloxyphenyl)-5-cyano-5-octyl-5,6-dihydro-4-H-cyclopenta[d]thiazole
2-(4-octyloxyphenyl)-5-cyano-5-ethyl-5,6-dihydro-4-H-cyclopenta[d]thiazole
2-(4-octyloxyphenyl)-5-cyano-5-propyl-5,6-dihydro-4-H-cyclopenta[d]thiazole
2-(4-octyloxyphenyl)-5-cyano-5-butyl-5,6-dihydro-4-H-cyclopenta[d]thiazole
2-(4-octyloxyphenyl)-5-cyano-5-pentyl-5,6-dihydro-4-H-cyclopenta[d]thiazole
2-(4-octyloxyphenyl)-5-cyano-5-hexyl-5,6-dihydro-4-H-cyclopenta[d]thiazole
2-(4-octyloxyphenyl)-5-cyano-5-heptyl-5,6-dihydro-4-H-cyclopenta[d]thiazole
2-(4-octyloxyphenyl)-5-cyano-5-octyl-5,6-dihydro-4-H-cyclopenta[d]thiazole

EXAMPLE 4

2.1 g of dicyclohexylcarbodiimide in 5 ml of methylene chloride are added to a mixture of 2.9 g of 5-cyano-5-n-heptyl-5,6-dihydro-4-H-cyclopenta[b]thiophene-2-carboxylic acid (which can be prepared from ethyl thiophene-2,3-dicarboxylate by saponification, decarboxylation, introduction of the cyano group, introduction of the n-heptyl group analogously to Example 3, Friedel-Crafts acetylation in the 2-position and a subsequent haloform reaction), 0.12 g of 4-dimethylaminopyridine, 2.0 g of 4-n-octylphenol and 20 ml of methylene chloride at 10°, with stirring, and the mixture is then stirred at room temperature for 15 hours. It is filtered with suction over silica gel and the solvent is evaporated to give, after recrystallization from ethanol, 4-n-octylphenyl 5-cyano-5-n-heptyl-5,6-dihydro-4-H-cyclopenta[b]thiophene-2-carboxylate.

The following compounds are prepared analogously:
4-propylphenyl 5-cyano-5-heptyl-5,6-dihydro-4-H-cyclopenta[b]thiophene-2-carboxylate
4-butylphenyl 5-cyano-5-heptyl-5,6-dihydro-4-H-cyclopenta[b]thiophene-2-carboxylate
4-pentylphenyl 5-cyano-5-heptyl-5,6-dihydro-4-H-cyclopenta[b]thiophene-2-carboxylate
4-hexylphenyl 5-cyano-5-heptyl-5,6-dihydro-4-H-cyclopenta[b]thiophene-2-carboxylate
4-heptylphenyl 5-cyano-5-heptyl-5,6-dihydro-4-H-cyclopenta[b]thiophene-2-carboxylate
4-propylphenyl 5-cyano-5-hexyl-5,6-dihydro-4-H-cyclopenta[b]thiophene-2-carboxylate
4-butylphenyl 5-cyano-5-hexyl-5,6-dihydro-4-H-cyclopenta[b]thiophene-2-carboxylate
4-pentylphenyl 5-cyano-5-hexyl-5,6-dihydro-4-H-cyclopenta[b]thiophene-2-carboxylate
4-hexylphenyl 5-cyano-5-hexyl-5,6-dihydro-4-H-cyclopenta[b]thiophene-2-carboxylate
4-heptylphenyl 5-cyano-5-hexyl-5,6-dihydro-4-H-cyclopenta[b]thiophene-2-carboxylate
4-octylphenyl 5-cyano-5-hexyl-5,6-dihydro-4-H-cyclopenta[b]thiophene-2-carboxylate
4-propylphenyl 5-cyano-5-pentyl-5,6-dihydro-4-H-cyclopenta[b]thiophene-2-carboxylate
4-butylphenyl 5-cyano-5-pentyl-5,6-dihydro-4-H-cyclopenta[b]thiophene-2-carboxylate
4-pentylphenyl 5-cyano-5-pentyl-5,6-dihydro-4-H-cyclopenta[b]thiophene-2-carboxylate
4-hexylphenyl 5-cyano-5-pentyl-5,6-dihydro-4-H-cyclopenta[b]thiophene-2-carboxylate
4-heptylphenyl 5-cyano-5-pentyl-5,6-dihydro-4-H-cyclopenta[b]thiophene-2-carboxylate
4-octylphenyl 5-cyano-5-pentyl-5,6-dihydro-4-H-cyclopenta[b]thiophene-2-carboxylate
4-propylphenyl 5-cyano-5-butyl-5,6-dihydro-4-H-cyclopenta[b]thiophene-2-carboxylate
4-butylphenyl 5-cyano-5-butyl-5,6-dihydro-4-H-cyclopenta[b]thiophene-2-carboxylate
4-pentylphenyl 5-cyano-5-butyl-5,6-dihydro-4-H-cyclopenta[b]thiophene-2-carboxylate
4-hexylphenyl 5-cyano-5-butyl-5,6-dihydro-4-H-cyclopenta[b]thiophene-2-carboxylate
4-heptylphenyl 5-cyano-5-butyl-5,6-dihydro-4-H-cyclopenta[b]thiophene-2-carboxylate
4-octylphenyl 5-cyano-5-butyl-5,6-dihydro-4-H-cyclopenta[b]thiophene-2-carboxylate
4-propylphenyl 5-cyano-5-propyl-5,6-dihydro-4-H-cyclopenta[b]thiophene-2-carboxylate
4-butylphenyl 5-cyano-5-propyl-5,6-dihydro-4-H-cyclopenta[b]thiophene-2-carboxylate
4-pentylphenyl 5-cyano-5-propyl-5,6-dihydro-4-H-cyclopenta[b]thiophene-2-carboxylate
4-hexylphenyl 5-cyano-5-propyl-5,6-dihydro-4-H-cyclopenta[b]thiophene-2-carboxylate
4-heptylphenyl 5-cyano-5-propyl-5,6-dihydro-4-H-cyclopenta[b]thiophene-2-carboxylate
4-octylphenyl 5-cyano-5-propyl-5,6-dihydro-4-H-cyclopenta[b]thiophene-2-carboxylate
4-propylphenyl 5-cyano-5ethyl-5,6-dihydro-4-H-cyclopenta[b]thiophene-2-carboxylate
4-butylphenyl 5-cyano-5-ethyl-5,6-dihydro-4-H-cyclopenta[b]thiophene-2-carboxylate
4-pentylphenyl 5-cyano-5-ethyl-5,6-dihydro-4-H-cyclopenta[b]thiophene-2-carboxylate
4-hexylphenyl 5-cyano-5-ethyl-5,6-dihydro-4-H-cyclopenta[b]thiophene-2-carboxylate
4-heptylphenyl 5-cyano-5-ethyl-5,6-dihydro-4-H-cyclopenta[b]thiophene-2-carboxylate
4-octylphenyl 5-cyano-5-ethyl-5,6-dihydro-4-H-cyclopenta[b]thiophene-2-carboxylate
4-octyloxyphenyl 5-cyano-5-heptyl-5,6-dihydro-4-H-cyclopenta[b]thiophene-2-carboxylate
4-heptyloxyphenyl 5-cyano-5-heptyl-5,6-dihydro-4-H-cyclepenta[b]thiophene-2-carboxylate
4-hexyloxyphenyl 5-cyano-5-heptyl-5,6-dihydro-4-H-cyclopenta[b]thiophene-2-carboxylate
4-pentyloxyphenyl 5-cyano-5-heptyl-5,6-dihydro-4-H-cyclopenta[b]thiophene-2-carboxylate
4-butyloxyphenyl 5-cyano-5-heptyl-5,6-dihydro-4-H-cyclopenta[b]thiophene-2-carboxylate
4-propyloxyphenyl 5-cyano-5-heptyl-5,6-dihydro-4-H-cyclopenta[b]thiophene-2-carboxylate The following examples relate to liquid crystal phases.

EXAMPLE A

A liquid crystal phase consisting of
12.8% of 3-fluoro-4-cyanophenyl 5-n-pentyl-5,6-dihydro-4-H-cyclopenta[b]thiophene-2-carboxylate,
5.1% of 3-fluoro-4-cyanophenyl 4-ethylbenzoate, 5.1% of 3-fluoro-4-cyanophenyl 4-propylbenzoate,
7.1% of 3-fluoro-4-cyanophenyl p-(trans-4-propylcyclohexyl)benzoate,
5.1% of 2-p-pentyloxyphenyl-5-pentylpyrimidine,
5.1% of 2-p-hexyloxyphenyl-5-hexylpyrimidine,
7.1% of trans-1-p-butyloxyphenyl-4-propylcyclohexane,
5.1% of 2-p-propylphenyl-5-propylpyrimidine,
5.1% of 2-p-propylphenyl-5-pentylpyrimidine,
15.2% of p-trans-4-propylcyclohexylphenyl butyrate,
14.2% of trans-1-p-propylphenyl-4-pentylcyclohexane,
4.1% of 4-(trans-4-propylcyclohexyl)-4'-(trans-4-propylcyclohexyl)-biphenyl,
5.1% of 4-(trans-4-pentylcyclohexyl)-4'-(trans-4-propylcyclohexyl)-biphenyl and
4.1% of 4-(trans-4-pentylcyclohexyl)-4'-(trans-4-pentylcyclohexyl)-biphenyl has a clear point of 67°.

EXAMPLE B

A liquid crystal phase consisting of
16% of 4-ethyl-4'-cyanobiphenyl,
20% of 4-butyl-4'-cyanobiphenyl,
18% of 4-pentyl-4'-cyanobiphenyl,
21% of 4-cyanobiphenyl trans-4-ethylcyclophexanecarboxylate,
9% of p-pentylphenyl p-methylbenzoate,
11% of p-pentylphenyl p-propylbenzoate and
5% of 4-n-heptylphenyl 5-n-pentyl-5,6-dihydro-4-H-cyclopenta[b]thiophene-2-carboxylate has a clear point of 63°.

EXAMPLE C

A liquid crystal phase consisting of
35% of 4-pentyl-4'-cyanobiphenyl,
17% of 4-heptyl-4'-cyanobiphenyl,
19% of p-trans-4-propylcyclohexyl-benzonitrile,
6% of 4-p-cyanophenyl-4'-pentylbiphenyl,
8% of 4-cyano-4'-(trans-4-pentylcyclohexyl)biphenyl,
5% of 4-n-heptylphenyl 5-n-pentyl-5,6-dihydro-4-H-cyclopenta[b]thiophene-2-carboxylate,
4% of 4-(trans-4-propylcyclohexyl)-2-fluoro-4'-(trans-4-propylcyclohexyl)biphenyl and
6% of 4-(trans-4-pentylcyclohexyl)-2-fluoro-4'(trans-4-propylcyclohexyl)biphenyl has a clear point of 80°.

EXAMPLE D

A liquid crystal phase consisting of
9% of r-1-cyano-cis-4-(trans-4-propylcyclohexyl)-1-propyl-cyclohexane,
5% of 2-(4-n-hexyloxyphenyl)-5-cyano-5-n-heptyl-5,6-dihydro-4-H-cyclopenta[d]thiazole,
28% of 1-(trans-4-propylcyclohexyl)-2-(2'-fluoro-4'-ethylbiphenyl-4-yl)ethane,
28% f 1-(trans-4-propylcyclohexyl)-2-(2'-fluoro-4'-pentylbiphenyl-4-yl)ethane,
26% of 1-(trans-4-pentylcyclohexyl)-2-(2'-fluoro-4'-ethylbiphenyl-4-yl)ethane and
4% of 4-(trans-4-propylcyclohexyl)-2-fluoro-4'-(trans-4-propylcyclohexyl)biphenyl has a clear point of 95°.

EXAMPLE E

A liquid crystal phase consisting of
8% of r-1-cyano-cis-4-(trans-4-ethylcyclohexyl)-1-propyl-cyclohexane,
6% of 4-n-octyloxyphenyl 5-cyano-5-n-heptyl-5,6-dihydro-4-H-cyclopenta[b]thiophene-2-carboxylate,
27% of 1-(trans-4-propylcyclohexyl)-2-(2'-fluoro-4'-ethylbiphenyl-4-yl)ethane,
27% of 1-(trans-4-propylcyclohexyl)-2-(2'-fluoro-4'-pentylbiphenyl-4-yl)ethane,
24% of 1-(trans-4-pentylcyclohexyl)-2-(2'-fluoro-4'-ethylbiphenyl-4-yl)ethane,
5% of 4-(trans-4-propylcyclohexyl)-2-fluoro-4'-(trans-4-propylcyclohexyl)biphenyl and
3% of 4-(trans-4-pentylcyclohexyl)-2-fluoro-4'-(trans-4-propylcyclohexyl)biphenyl has a clear point of 93°.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A liquid crystal phase comprising at least two liquid crystal components, wherein at least one liquid crystal component is a heterocyclic compound having the structure wing group-ring-(bridge member-ring)$_{(1-3)}$-wing group, wherein at least one ring is of the formula

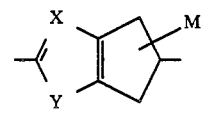

wherein
M is H, CN, NCS, halogen or alkyl of 1–5 C atoms,
X is CR$^4$ or N,
Y is CHR$^4$, O, S or NR$^5$,
R$^4$ is H, alkyl of 1–15 C atoms, halogen or cyano and
R$^5$ is H, alkyl of 1–15 C atoms, with the proviso that when Y=CHR$^4$,
X is N.

2. A liquid crystal phase of claim 1, wherein said at least one component is of the formula

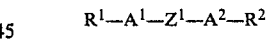

wherein
R$^1$ and R$^2$ each independently of one another are an unsubstituted alkyl group of 1–15 C atoms, or such an alkyl group wherein one or two CH$_2$ groups are replaced each by one of the groups —O—, —CO—, —CHHalogen—, —CH—CN—, —O—CO—, —CO—O— or —CH=CH—, two hetero atoms not being linked directly to one another, and one of the radicals R$^1$ and R$^2$ can also be H, F, Cl, Br, —CN, —NCS or R$^3$—(A$^3$)$_p$—Z$^2$,
A$^1$ is —A—, —A$^4$—Z$^3$—A— or —A—Z$^3$—A$^4$—,
A$^2$, A$^3$ and A$^4$ are each independently 1,4-phenylene which is unsubstituted or substituted by one or more of F, Cl, CH$_3$, Cn or a combination thereof, and wherein one or two CH groups can also be replaced by N atoms; 1,4-cyclohexylene which is unsubstituted or substituted by one or more of F, Cl, CH$_3$, Cn or a combination thereof, and wherein one or two non-adjacent CH$_2$ groups can also be replaced by O, S or a combination thereof; piperidine-1,4-diyl; 1,4-bicyclo(2,2,2)-octylene; or decahydronaphthalene-2,6-diyl or 12,3,4-tetrahydronaphthalene-2,6-diyl, each of which is unsubstituted or substituted by CN, $Z^1$, $Z^2$ and $Z^3$ are each independently —CO—O—, —O—CO—, —OCH$_2$—, —CH$_2$O—, —CH$_2$CH$_2$—, substituted ethylene or a single bond, $R^3$ is H, an unsubstituted alkyl group of 1-15 C atoms, or such an alkyl group wherein one or two CH$_2$ groups are replaced each by one of the groups —O—, —CO—, —CHHalogen—, —CH—CN—, —O—CO—, —CO—O— or —CH=CH—, two hetero atoms not being linked directly to one another; F; Cl; Br; —NCS; or —CN, p is 1 or 2 and A is the structural element

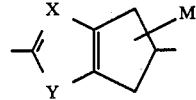

wherein

M is H, Cn, NCS, halogen or an alkyl group of 1-5 C atoms,

X is CR$^4$ or N,

Y is CHR$^4$, O, S or NR$^5$,

R$^4$ is H, alkyl of 1-15 C atoms, halogen or cyano and

R$^5$ is H or alkyl of 1-15 C atoms, and wherein, when p=2, the groups A$^3$ can be identical or different, with the proviso that when Y=CHR$^4$, X is N.

3. A phase of claim 2, wherein said component is of the formula $R^1$—A—$Z^1$—$A^2$—$R^2$, $R^1$—A—$A^2$—$R^2$, $R^1$—$A^4$—$Z^3$—A—$Z^1$—$A^2$—$R^2$, $R^1$—$A^4$—A—$A^2$—$R^2$, $R^1$—$A^4$—A—$Z^1$—$A^2$—$R^2$, $R^1$—$A^4$—$Z^3$—A—$A^2$—$R^2$, $R^1$—A—$Z^1$—$A^2$—$Z^2$—$A^3$—$R^3$, $R^1$—A—$A^4$—$A^2$—$R^2$, $R^1$—A—$Z^3$—$A^4$—$A^2$—$R^2$, $R^1$—A—$A^2$—$Z^2$—$A^3$—$R^3$, $R^3$—$A^3$—$A^3$—$Z^2$—A—$Z^1$—$A^2$—$R^2$, $R^3$—$A^3$—$A^4$—$Z^3$—A—$Z^1$—$A^2$—$R^2$, $R^3$—$A^3$—$A^3$—$Z^2$—A—$A^2$—$R^2$, $R^3$—$A^3$—$A^4$—A—$A^2$—$R^2$, $R^3$—$A^3$—$A^3$—A—$Z^1$—$A^2$—$R^2$, $R^1$—A—$Z^1$—$A^2$—$Z^2$—$A^3$—$A^3$—$R^3$, $R^1$—A—$A^2$—$A^3$—$A^3$—$R^3$, $R^1$—A—$Z^1$—$A^2$—$A^3$—$A^3$—$R^3$, $R^1$—A—$A^2$—$Z^2$—$A^3$—$A^3$—$R^3$, $R^3$—$A^3$—$Z^2$—$A^4$—$Z^3$—A—$Z^1$—$A^2$—$R^2$, $R^1$—$A^4$—A—$Z^1$—$A^2$—$Z^2$—$A^3$—$R^3$, $R^3$—$A^3$—$Z^2$—$A^4$—A—$Z^1$—$A^2$—$R^3$, $R^1$—$A^4$—A—$A^2$—$Z^2$—$A^3$—$R^3$, $R^1$—A—$Z^3$—$A^4$—$Z^1$—$A^2$—$Z^2$—$A^3$—$R^3$, $R^1$—A—$Z^3$—$A^4$—$A^2$—$Z^2$—$A^3$—$R^3$, $R^1$—A—$A^4$—$Z^1$—$A^2$—$Z^2$—$A^3$—$R^3$, $R^1$—A—$A^4$—$A^2$—$Z^2$—$A^3$—$R^3$, $R^1$—A—$Z^3$—$A^4$—$Z^1$—$A^2$—$Z^2$—$A^3$—$A^3$—$R^3$, $R^1$—A—$Z^3$—$A^4$—$Z^1$—$A^2$—$A^3$—$A^3$—$R^3$, $R^1$—A—$Z^3$—$A^4$—$A^2$—$Z^2$—$A^3$—$A^3$—$R^3$, $R^1$—A—$A^4$—$Z^1$—$A^2$—$Z^2$—$A^3$—$A^3$—$R^3$, $R^1$—A—$A^4$—$A^2$—$A^3$—$A^3$—$R^3$, $R^1$—A—$Z^3$—$A^4$—$A^2$—$A^3$—$A^3$—$R^3$, $R^1$—A—$A^4$—$Z^1$—$A^2$—$A^3$—$A^3$—$R^3$, $R^1$—A—$A^4$—$A^2$—$Z^2$—$A^3$—$A^3$—$R^3$, $R^3$—$A^3$—$A^3$—$Z^2$—$A^4$—$Z^3$—A—$Z^1$—$A^2$—$R^2$, $R^1$—$A^4$—$Z^3$—A—$Z^1$—$A^2$—$A^3$—$A^3$—$R^3$, $R^R$—$A^4$—$Z^3$—A—$A^2$—$Z^2$—$A^3$—$A^3$—$R^3$, $R^1$—$A^4$—A—$Z^1$—$A^2$—$Z^2$—$A^3$—$A^3$—$R^3$, $R^3$—$A^3$—$A^3$—$A^4$—A—$A^2$—$R^2$, $R^1$—$A^4$—A—$A^2$—$Z^2$—$A^3$—$A^3$—$R^3$, $R^1$—$A^4$—$Z^3$—A—$A^2$—$A^3$—$A^3$—$R^3$, $R^3$—$A^3$—$A^3$—$A^4$—$Z^3$—A—$A^2$—$R^2$, $R^3$—$A^3$—$A^3$—A—$A^4$—$A^2$—$R^2$, $R^3$—$A^3$—$A^3$—$Z^2$—A—$Z^3$—$A^4$—$Z^1$—$A^2$—$R^2$, $R^3$—$A^3$—$A^3$—$Z^2$—A—$A^4$—$Z^1$—$A^2$—$R^2$, $R^3$—$A^3$—$A^3$—$Z^2$—A—$Z^3$—$A^4$—$A^2$—$R^2$, $R^3$—$A^3$—$A^3$—A—$Z^3$—$A^4$—$Z^1$—$A^2$—$R^2$, $R^3$—$A^3$—$A^3$—A—$Z^3$—$A^4$—$A^2$—$R^2$ or $R^3$—$A^3$—$A^3$—A—$A^4$—$Z^1$—$A^2$—$R^2$.

4. A phase of claim 2 wherein $R^1$, $R^2$ and $R^3$ are alkyl, alkoxy, CN, F or Cl.

5. A phase of claim 2 wherein $A^2$, $A^3$ and $A^4$ are 1,4-phenylene, 1,4-cyclohexylene, 1,3-dioxane-2,5-diyl or pyrimidine-2,5-diyl, unsubstituted or monosubstituted by F, Cl, CH$_3$ or CN.

6. A phase of claim 2, wherein Y is S, O or NR$^5$.

7. A phase of claim 2, wherein A is of the formula

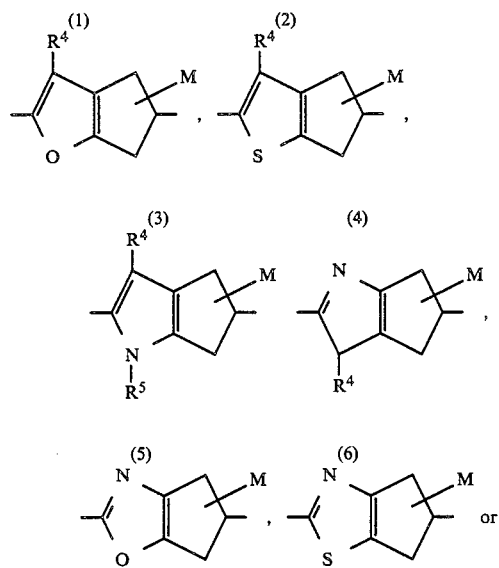

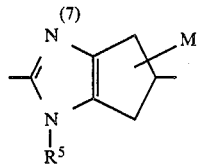

8. A phase of claim 7, wherein A is of the formula (2) or (6).

9. A phase of claim 2 wherein said at least one component is optically active.

10. In an electrooptical display device, comprising a liquid crystal phase, the improvement wherein said phase is one of claim 8.

11. In an electrooptical display device, comprising a liquid crystal phase, the improvement wherein said phase is one of claim 1.

12. In an electrooptical display device comprising a liquid crystal phase, the improvement wherein said phase is one of claim 2.

* * * * *

UNITED STATES PATENT AND TRADEMARK OFFICE
CERTIFICATE OF CORRECTION

PATENT NO. : 4,853,149

DATED : AUGUST 1, 1989

INVENTOR(S) : KRAUSE ET AL

It is certified that error appears in the above-identified patent and that said Letters Patent is hereby corrected as shown below:

Column 26, claim 3, line 36: reads "$R^R-A^4-Z^3-A-A^2-Z^2-A^3-A^3-R^3$,"

should read -- $R^1-A^4-Z^3-A-A^2-Z^2-A^3-A^3-R^3$, --

Signed and Sealed this

Twelfth Day of June, 1990

Attest:

HARRY F. MANBECK, JR.

*Attesting Officer*      *Commissioner of Patents and Trademarks*